US011058320B2

(12) United States Patent
Meftah et al.

(10) Patent No.: US 11,058,320 B2
(45) Date of Patent: Jul. 13, 2021

(54) METHOD AND APPARATUS FOR DETERMINING AT LEAST ONE OF A POSITION AND AN ORIENTATION OF A WEARABLE DEVICE ON A SUBJECT

(71) Applicant: KONINKLIJKE PHILIPS N.V., Eindhoven (NL)

(72) Inventors: Mohammed Meftah, Tilburg (NL); Nicole Hijnen, Eindhoven (NL); Vincent Alexander Rudolf Aarts, Eindhoven (NL); Michael Heesemans, Eindhoven (NL); Rene Martinus Maria Derkx, Eindhoven (NL); Teun Van Den Heuvel, Deventer (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 16/096,571

(22) PCT Filed: Apr. 28, 2017

(86) PCT No.: PCT/EP2017/060141
§ 371 (c)(1),
(2) Date: Oct. 25, 2018

(87) PCT Pub. No.: WO2017/191036
PCT Pub. Date: Nov. 9, 2017

(65) Prior Publication Data
US 2019/0133488 A1 May 9, 2019

(30) Foreign Application Priority Data
May 4, 2016 (EP) .................................. 16168261

(51) Int. Cl.
*A61B 5/06* (2006.01)
*A61B 5/00* (2006.01)
(Continued)

(52) U.S. Cl.
CPC ................ *A61B 5/06* (2013.01); *A61B 5/318* (2021.01); *A61B 5/349* (2021.01); *A61B 5/6833* (2013.01);
(Continued)

(58) Field of Classification Search
CPC ....... A61B 5/06; A61B 5/0452; A61B 5/0402; A61B 5/6833; A61B 5/6823; A61B 5/7235; A61B 5/1114; A61B 2560/0412
See application file for complete search history.

(56) References Cited

U.S. PATENT DOCUMENTS

| 6,282,440 B1 | 8/2001 | Brodnick et al. |
| 2008/0281234 A1 | 11/2008 | Goris et al. |

(Continued)

FOREIGN PATENT DOCUMENTS

| EP | 2578141 A1 | 4/2013 |
| WO | 2012014110 A2 | 2/2012 |

(Continued)

OTHER PUBLICATIONS

VitalConnect, VitalPatch, "The Most discrete and advanced patient monitoring device available", http://www.vitalconnect.com/healthpatch-md, 2 pages, (Abstract).

*Primary Examiner* — Mallika D Fairchild (57) ABSTRACT

There is provided a method and apparatus for determining at least one of a position and an orientation of a wearable device on a subject. At least one physiological characteristic signal is acquired from a subject (402). The acquired at least one physiological characteristic signal from the subject has one or more characteristics indicative of at least one of a position and an orientation of a wearable device on the subject. The at least one of the position and orientation of the wearable device on the subject is determined based on the one or more characteristics indicative of the at least one of (Continued)

the position and orientation of the wearable device on the subject (404).

15 Claims, 8 Drawing Sheets

(51) Int. Cl.
*A61B 5/318* (2021.01)
*A61B 5/349* (2021.01)
*A61B 5/11* (2006.01)

(52) U.S. Cl.
CPC ........... *A61B 5/1114* (2013.01); *A61B 5/6823* (2013.01); *A61B 5/7235* (2013.01); *A61B 2560/0412* (2013.01)

(56) References Cited

U.S. PATENT DOCUMENTS

| | | | |
|---|---|---|---|
| 2009/0076340 A1* | 3/2009 | Libbus | A61B 5/061 600/301 |
| 2012/0072168 A1 | 3/2012 | Yin et al. | |
| 2014/0032165 A1 | 1/2014 | Sarrafzadeh et al. | |
| 2014/0343372 A1 | 11/2014 | Ahmed et al. | |
| 2016/0279405 A1* | 9/2016 | Riley | A61N 1/3925 |
| 2017/0055869 A1* | 3/2017 | Shin | A61B 5/04288 |
| 2017/0265838 A1* | 9/2017 | Schulhauser | A61B 7/04 |

FOREIGN PATENT DOCUMENTS

| | | |
|---|---|---|
| WO | 2013126684 A1 | 8/2013 |
| WO | 2016040879 A1 | 3/2016 |

\* cited by examiner

METHOD AND APPARATUS FOR DETERMINING AT LEAST ONE OF A POSITION AND AN ORIENTATION OF A WEARABLE DEVICE ON A SUBJECT

This application is the U.S. National Phase application under 35 U.S.C. § 371 of International Application No. PCT/EP2017/060141, filed on Apr. 28, 2017, which claims the benefit of European Application Serial No. 16168261.2 filed May 4, 2016. These applications are hereby incorporated by reference herein.

TECHNICAL FIELD OF THE INVENTION

The invention relates to the field of wearable devices and, in particular, relates to a method and apparatus for determining at least one of a position and an orientation of a wearable device on a subject.

BACKGROUND TO THE INVENTION

The health of a subject often needs to be monitored and this can be achieved through use of a monitoring device. A monitoring device can comprise sensors for monitoring the health of a subject through physiological characteristic (i.e. vital sign) measurements. Advances in technology have resulted in monitoring devices becoming smaller and more unobtrusive. For example, some monitoring devices have been designed to be worn by the subject. In other words, a subject can now wear a monitoring device on their body as a wearable device. The advances in wearable devices mean that it is possible to monitor a subject at any location, whether that be at a professional healthcare facility (such as a hospital, an intensive care unit ICU, or similar) or at home.

Some wearable devices have been designed in the form of a patch having an adhesive surface that can adhere to the skin of a subject. The patch may be a disposable patch that can be worn by the subject for a certain number of days. However, the removal and attachment of the patch can cause skin irritation, which can be worsened if a patch is continuously applied at the same location on the body of the subject. Therefore, it is preferred to have multiple different locations on the body of the subject to which the wearable device can be applied.

However, in order to interpret measured data in the correct way, the sensor system needs to know the position at which the wearable device (and thus any sensors of the wearable device) is applied on the body of the subject and also the orientation (e.g. the polarity) of the wearable device after application of the wearable device to the body of the subject. This is especially the case when the wearable device contains a tri-axial accelerometer for the measurement of posture, energy expenditure and gait.

The requirement for the system to know the position and orientation of the wearable device on the body of the subject means that a calibration procedure is necessary after application of the wearable device to the body of the subject. Currently, calibration procedures require manual effort from a user of the system (for example, from the subject themselves or another user such as a healthcare professional or caregiver). Specifically, a user of the system is required to manually enter the position and orientation of the wearable device on the body of the subject via an input device (such as a tablet, a personal computer, a smartphone, or similar). Also, current calibration procedures require the subject to be positioned upright (such as in a standing position, or walking) for a predetermined time period while calibration is performed.

However, the current calibration procedures that require the subject to be in an upright position are not feasible in case the subject is unwell, unable to stand up, or confined to a laying position. Also, current calibration procedures that require the manual input of position and orientation information are prone to error and inefficient. For in-hospital use, this can be particularly disadvantageous since time is often limited and, in some cases, critical. In a home situation, inexperienced users (e.g. health coaches or the subject themselves) may be required to attach the wearable device and input the position and orientation information themselves into an often complex system. This can prove to be particularly difficult for the sick and elderly. The inexperienced users may have difficulty operating the system or may even forget to perform the calibration procedure. Thus, current calibration procedures are often not feasible, are prone to error and are inefficient.

There is therefore a need for an automated determination of position and orientation of a wearable device (such as a patch) on a subject that can be used to enable an automated calibration. By minimising, or even eliminating, the need for human interaction in the determination of position and orientation of a wearable device on the body of a subject, it will be possible to provide more reliable and reproducible signals, measurements, data and readings from sensors contained in the wearable device.

US 2014/0032165 A1 discloses a method for determining a location of a sensor without requiring data input regarding device placement. The method uses acceleration data associated with a monitoring device to determine where it has been applied on the body since different parts of the body can exhibit different activity characteristics. Upon estimation of the location of the sensor on the body, stationary data for accelerometers can be used to derive the orientation of the sensor on the body, such as the relative positioning of the sensor relative to the body part to which the sensor is applied.

However, it is not always possible to reliably obtain the position and orientation of a device on the body of the subject from accelerometer data in certain situations (such as where the subject is motionless, moving slowly, or not walking). Moreover, it is not possible to determine the position of the device on the body of the subject with sufficient accuracy to obtain an exact location (for example, whether the device is on front of the chest or on the side of the chest). It is also not possible to determine an accurate three-dimensional orientation of the device on the subject in certain situations. For example, if calibration of the device is performed when the subject is walking and the subject is bent over while walking, estimation of the axes to be used for the three-dimensional orientation measurement will be incorrect. This is particularly problematic in the case of elderly subjects, where it is often difficult to reliably detect walking (for example, due to the subject walking slowly, shuffling, or being supported).

Therefore, there is a need for an improved method and apparatus that more reliably and accurately determines at least one of a position and an orientation of a wearable device on a subject.

SUMMARY OF THE INVENTION

As noted above, a limitation with existing approaches is that it is not possible to reliably obtain the position and orientation with sufficient accuracy. The invention provides an improved method and apparatus for determining at least one of (i.e. one of or both) a position and an orientation of a wearable device on a subject. In other words, the invention relates to an improved method and apparatus for determining a position and/or an orientation of a wearable device on a subject.

Therefore, according to a first aspect of the invention, there is provided a method for determining at least one of a position and an orientation of a wearable device on a subject, the method comprising: acquiring at least one physiological characteristic signal from a subject, the acquired at least one physiological characteristic signal from the subject having one or more characteristics indicative of at least one of a position and an orientation of a wearable device on the subject; and determining the at least one of the position and orientation of the wearable device on the subject based on the one or more characteristics indicative of the at least one of the position and orientation of the wearable device on the subject.

In some embodiments, determining the at least one of the position and orientation of the wearable device on the subject may comprise: comparing the one or more characteristics of the acquired at least one physiological characteristic signal from the subject to a plurality of predefined characteristics, each of the plurality of predefined characteristics associated with at least one of a predefined position and orientation of the wearable device; and determining the at least one of the position and orientation of the wearable device on the subject based on the comparison.

In some embodiments, determining the at least one of the position and orientation of the wearable device on the subject based on the comparison may comprise: determining which of the plurality of predefined characteristics match or most closely match the one or more characteristics of the acquired at least one physiological characteristic signal; and determining the at least one of the position and orientation of the wearable device on the subject as the at least one of the predefined position and orientation associated with the predefined characteristics determined to match or most closely match the one or more characteristics of the acquired at least one physiological characteristic signal.

In some embodiments, determining the at least one of the position and orientation of the wearable device on the subject based on the comparison may comprise interpolating the plurality of predefined characteristics and the at least one of the associated predefined positions and orientations of the wearable device to determine the at least one of the position and orientation of the wearable device on the subject.

In some embodiments, the at least one physiological characteristic signal may comprise an electrocardiogram signal.

In some embodiments, the one or more characteristics indicative of the at least one of the position and orientation of the wearable device on the subject may comprise one or more of a morphology of the electrocardiogram signal, an amplitude of the electrocardiogram signal, and a polarity of the electrocardiogram signal.

In some embodiments, the at least one physiological characteristic signal may comprise, or may further comprise, an acoustic signal.

In some embodiments, the one or more characteristics of the acoustic signal indicative of the at least one of the position and orientation of the wearable device on the subject may comprise one or more of a frequency of the acoustic signal, a power of the acoustic signal, a phase of the acoustic signal, and a temporal feature of the acoustic signal.

In some embodiments, the method may further comprise outputting a signal indicative of the determined at least one of the position and orientation of the wearable device on the subject.

In some embodiments, the method may further comprise calibrating the wearable device based on the determined at least one of the position and orientation of the wearable device on the subject.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method described above.

According to a third aspect of the invention, there is provided an apparatus for determining at least one of the position and an orientation of a wearable device on a subject, the apparatus comprising a control unit configured to: acquire at least one physiological characteristic signal from a subject, the acquired at least one physiological characteristic signal from the subject having one or more characteristics indicative of at least one of a position and an orientation of a wearable device on the subject; and determine the at least one of the position and orientation of the wearable device on the subject based on the one or more characteristics indicative of the at least one of the position and orientation of the wearable device on the subject.

In some embodiments, the control unit may be configured to acquire the at least one physiological characteristic signal from the subject by controlling at least one physiological characteristic sensor to acquire the at least one physiological characteristic signal.

In some embodiments, the wearable device may comprise the at least one physiological characteristic sensor.

In some embodiments, the at least one physiological characteristic sensor may comprise one or more of: an electrocardiogram physiological characteristic sensor and an acoustic physiological characteristic sensor.

Therefore, position and orientation of a wearable device on a subject can be extracted from physiological characteristic signals that have characteristics specific to particular positions and orientations. This provides an automatic, more reliable and more accurate determination of the position and orientation of a wearable device on a subject to thereby provide more reliable and more accurate measurements from sensors in, or on, the wearable device.

There is thus provided an improved method and apparatus for determining at least one of (i.e. one of or both) a position and an orientation of a wearable device on a subject. In other words, there is provided an improved method and apparatus for determining a position and/or an orientation of a wearable device on a subject.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides an improved method and apparatus for determining at least one of (i.e. one of or both) a position and an orientation of a wearable device on a subject. In other words, the invention provides an improved method and apparatus for determining a position and/or an orientation of a wearable device on a subject. The device can be any device that is designed to be worn by a subject (such as a user, a patient, or any other subject). It will be understood that the position of the wearable device on the subject is the actual or absolute position (or location) on the body of the subject at which the device is being worn or at which the device has been applied. For example, it is possible to determine whether the device is at the centre of the chest, the side of the chest, or any other position (or location) on the body of the subject. The wearable device can comprise at least one physiological characteristic (or vital signs) sensor.

Figure 1:
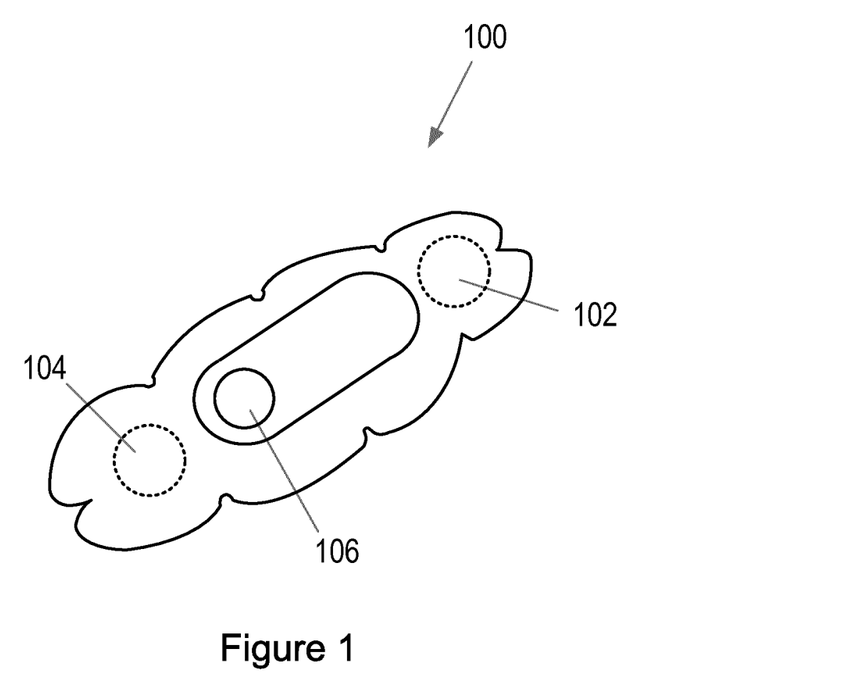
FIG. 1 is an illustration of an exemplary wearable device according to an embodiment.

FIG. 1 illustrates an exemplary device 100 that is designed to be worn by a subject according to an embodiment. In this embodiment, the wearable device 100 is in the form of a pad (such as a strip or patch). The pad may be formed of a flexible material such as a polyolefin foam, polyurethane, or any other flexible material. The pad may comprise an adhesive (such as a tacky or sticky) surface that can adhere to the skin of a subject. In this way, the wearable device can be worn by the subject. The wearable device can comprise at least one (and any number of) physiological characteristic sensor. The physiological characteristic sensors can be integrated in the wearable device or can be attached to the wearable device. In this exemplary embodiment, the wearable device 100 comprises two physiological characteristic sensors 102, 104 that are integrated into the wearable device 100. The wearable device 100 also comprises a marker 106 that can be used to distinguish between different orientations of the wearable device 100 when applied to a subject.

Although an example of the form that the wearable device may take has been provided, it will be appreciated that the wearable device is not limited to this form and other forms of device designed to be worn by a subject are also possible. Also, although an example number and arrangement of physiological characteristic sensors have been provided, it will be understood that other numbers and arrangements of physiological characteristic sensors are possible.

The wearable device can be a certain type of device (for example, the wearable device may have a certain function). In some embodiments, the device is a health monitoring device. A health monitoring device can be configured to monitor the physiological characteristics of a subject wearing the device for the purpose of monitoring the health of the subject. In some embodiments, the device is an activity monitoring device. An activity monitoring device can be configured to monitor the physiological characteristics of a subject wearing the device for the purpose of monitoring the subject during exercise programs, during walking (e.g. pedometers), during general daily activities, or to detect the occurrence of specific events such as the user falling and/or the user getting out of bed. In some embodiments, the device is a support device. A support device can be configured to monitor the physiological characteristics of a subject wearing the device for the purpose of transmitting a signal to another device (such as a device of a care giver, a healthcare provider, a health coach, a family member, an emergency contact person, or any other person) indicating that the subject wearing the device requires assistance or to raise an alarm. In some embodiments, the device may be provided with one or more of the health monitoring, activity monitoring, and support features described.

Although examples of the type of device have been provided, it will be appreciated that the device is not limited to these types of device and the any other type of device suitable to be worn by the user is also possible or any device for which it is desirable or useful to determine at least one of the position and orientation of the wearable device on the subject.

Figure 2:
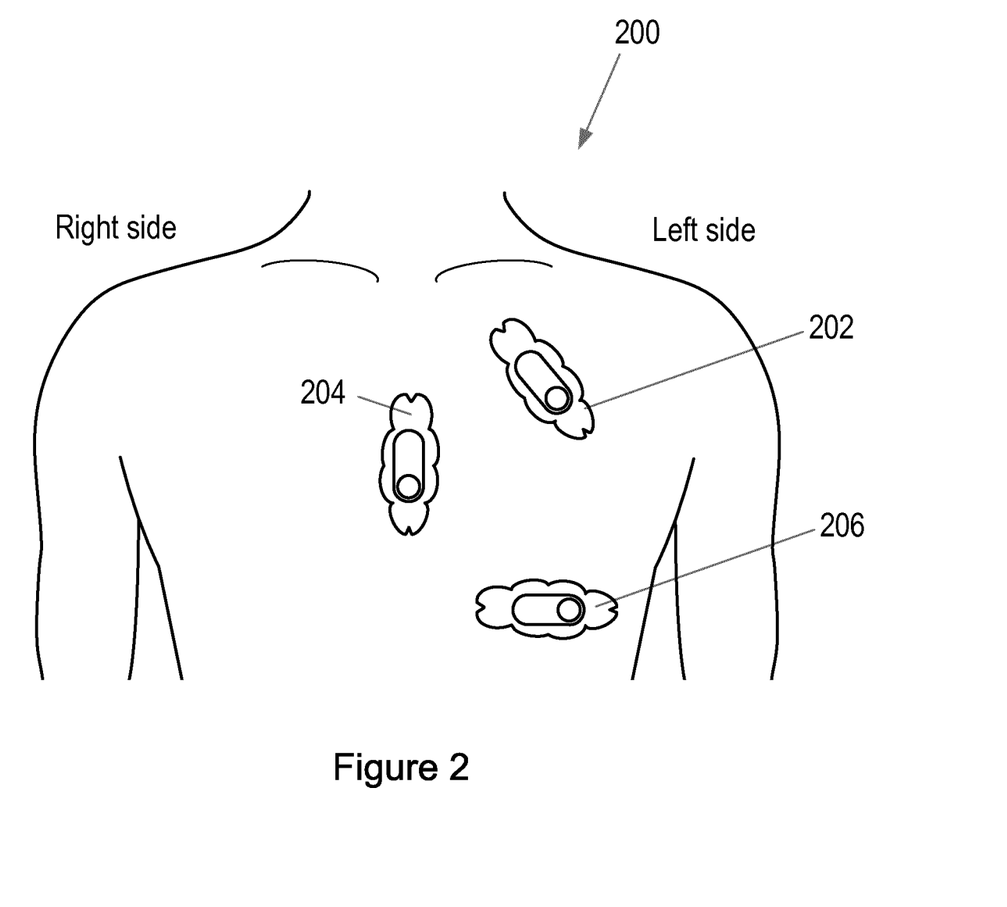
FIG. 2 is an illustration of a subject wearing an exemplary wearable device according to an embodiment.

FIG. 2 shows an exemplary embodiment illustrating a wearable device worn by a subject 200 at different positions and orientations 202, 204, 206. In this exemplary embodiment, it is illustrated that the wearable device can be worn by the subject 200 at a first position and orientation 202, at a second position and orientation 204, or at a third position and orientation 206 on the body of the subject 200. Although examples have been provided for different positions and orientations in which the wearable device may be worn by the subject, it will be understood that a wearable device can be worn in any position, at any orientation and on any part of the body of the subject. A wearable device is positioned to make contact with the skin of the subject. In this way, any physiological characteristic sensors of the wearable device can acquire one or more physiological characteristic signals from the subject. A wearable device may comprise one or a plurality of physiological characteristic sensors.

Figure 3:
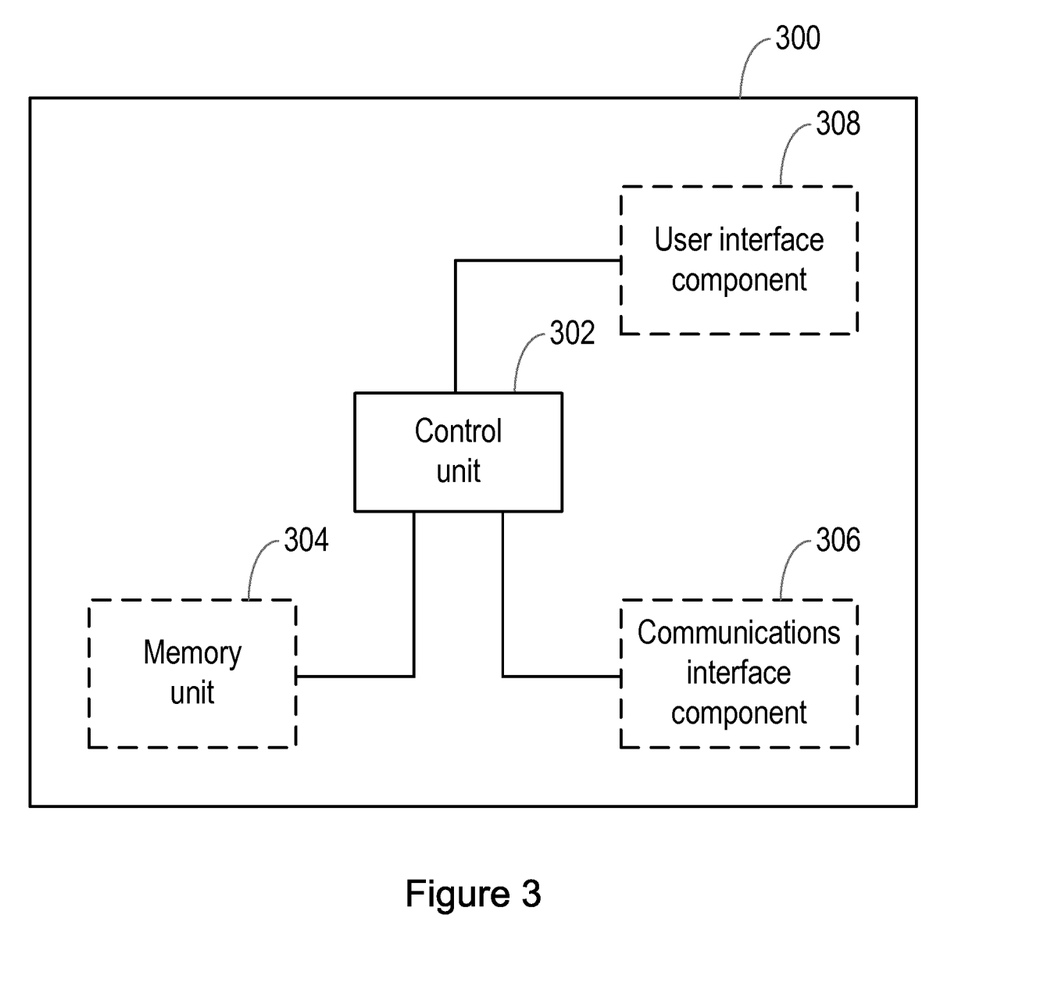
FIG. 3 is a block diagram of an apparatus according to an embodiment.

FIG. 3 shows a block diagram of an apparatus 300 according to an embodiment of that can be used for determining at least one of a position and an orientation of a wearable device on a subject (i.e. for determining a position and/or an orientation of a wearable device on a subject).

The apparatus 300 comprises a control unit 302 that controls the operation of the apparatus 300 and that can implement the method described herein. The control unit 302 can comprise one or more processors, processing units, multi-core processors or modules that are configured or programmed to control the apparatus 300 in the manner described herein. In particular implementations, the control unit 302 can comprise a plurality of software and/or hardware modules that are each configured to perform, or are for performing, individual or multiple steps of the method according to embodiments of the invention.

In some embodiments, the apparatus 300 is external to (i.e. separate to or remote from) the wearable device. In these embodiments, the apparatus 300 may comprise a communications interface component 306 for enabling the apparatus 300 to communicate with any sensors and devices that are external to the apparatus 300 (such as any physiological characteristic sensors of one or more wearable devices). The communications interface component 306 may communicate with any sensors and devices wirelessly or via a wired connection.

In other embodiments, the apparatus 300 is a wearable device. In other words, a wearable device itself may comprise the control unit 302.

Briefly, the control unit 302 is configured to acquire at least one physiological characteristic signal from a subject. The at least one physiological characteristic signal acquired from the subject is at least one physiological characteristic signal that has one or more characteristics indicative of at least one of a position and an orientation of a wearable device on the subject (i.e. indicative of a position and/or an orientation of a wearable device on a subject). The control unit 302 is configured to determine the at least one of the position and orientation of the wearable device on the subject based on the one or more characteristics indicative of the at least one of the position and orientation of the wearable device on the subject. In other words, the control unit 302 is configured to determine the position and/or the orientation of the wearable device on the subject based on the one or more characteristics.

In some embodiments, the control unit 302 is configured to acquire the at least one physiological characteristic signal from the subject by controlling at least one physiological characteristic sensor to acquire the at least one physiological characteristic signal. As mentioned earlier, a wearable device can comprise at least one physiological characteristic sensor and the control unit 302 may be configured to acquire the at least one physiological characteristic signal from the subject by controlling the at least one physiological characteristic sensor of one or more wearable devices to acquire the at least one physiological characteristic signal.

Where the apparatus 300 is external to (i.e. separate to or remote from) a wearable device, the control unit 302 of the apparatus 300 controls the one or more physiological characteristic sensors of one or more wearable devices to acquire the at least one physiological characteristic signal from the subject via a wired or wireless connection. Where the apparatus 300 is a wearable device (i.e. where a wearable device comprises the control unit 302), the control unit 302 controls the one or more physiological characteristic sensors of the wearable device to acquire the at least one physiological characteristic signal from the subject via an internal connection.

A wearable device can comprise any number of physiological characteristic sensors. For example a wearable device may comprise one physiological characteristic sensor, two physiological characteristic sensors, three physiological characteristic sensors, four physiological characteristic sensors, or any other number of physiological characteristic sensors. A physiological characteristic (or vital signs) sensor may be any sensor suitable to acquire at least one physiological characteristic signal from a subject. For example, a physiological characteristic sensor can comprise one or more of a heart rate sensor (such as an electrocardiogram ECG sensor, a photoplethysmography PPG sensor, a phonocardiography PCG sensor, or any other heart rate sensor), a vibration detection sensor or an acoustic physiological characteristic sensor (such as such as microphone, a capacitive micromachined ultrasonic transducer CMUT sensor, an accelerometer, a strain gauge, a responsive material, or any other acoustic physiological characteristic sensor), a skin conductivity sensor, a muscle activity sensor (such as an electromyography EMG sensor), a temperature sensor (such as a skin temperature sensor), a respiratory rate sensor, and any other type of sensor suitable to acquire one or more physiological characteristic signals from a subject.

In some embodiments, a physiological characteristic sensor in the form of a heart rate sensor may be used, where the control unit 302 controls the heart rate sensor to acquire signals indicative of a physiological characteristic of the subject. In this embodiment, the signals indicative of a physiological characteristic of the subject are heart rate signals. The heart rate sensor may be any type of heart rate sensor.

In one example, the heart rate sensor is an electrocardiogram (ECG) sensor and the heart rate signal of the subject may be acquired from an ECG signal (i.e. a signal indicating the electrical activity of the heart) measured by the ECG sensor. An ECG signal is received from the subject when a wearable device comprising an ECG sensor is worn by the subject. The ECG sensor may comprise one or more electrodes.

In another example, the heart rate sensor is a photoplethysmography (PPG) sensor and the heart rate signal of the subject may be acquired from a PPG signal measured by the PPG sensor. A PPG signal is received from the subject when a wearable device comprising a PPG sensor is worn by the subject. The PPG sensor may comprise one or more light sources (such as LEDs) operating at specific frequencies and one or more light detectors (such as photo-diodes), which react to the light that is either reflected or transmitted when the PPG sensor is in contact with the skin of the subject.

In another example, the heart rate sensor is a phonocardiography (PCG) sensor and the heart rate signal of the subject may be acquired from a PCG signal measured by the PCG sensor. A PCG signal is received from the subject when a wearable device comprising a PCG sensor is worn by the subject. The PCG sensor may comprise one or more vibration transducers (or microphones), which detect acoustic signals when the PCG sensor is in contact with the skin of the subject.

In some embodiments, a physiological characteristic sensor in the form of a skin conductivity sensor may be used, where the control unit 302 controls the skin conductivity sensor to acquire signals indicative of a physiological characteristic of the subject. In this embodiment, the signals indicative of physiological characteristic of the subject are skin conductivity signals (i.e. galvanic skin response signals). The skin conductivity sensor may be in the form of a pair of electrodes that are placed in a wearable device to contact with the skin of the subject. An electrical current may be applied through one of the electrodes and the resistance of the skin measured, or the voltage between the electrodes can be measured.

In some embodiments, a physiological characteristic sensor in the form of an acoustic physiological characteristic sensor may be used, where the control unit 302 controls the acoustic physiological characteristic sensor to acquire signals indicative of at least one physiological characteristic of the subject. In other words, the control unit 302 may control at least one acoustic physiological characteristic sensor to acquire body sounds or vibrations from the subject wearing the wearable device. In some embodiments, a single acoustic physiological characteristic sensor may be used. In other embodiments, a plurality of (or an array of) acoustic physiological characteristic sensors may be used, which enable the direction of an acquired acoustic signal to be identified. The acoustic physiological characteristic sensors may be all of the same type, or at least some may be of a different type. The acoustic physiological characteristic signals acquired from an acoustic physiological characteristic sensor are indicative of body vibrations (for example, vibrations originating from organs such as the heart, lungs, or other organs)

and can be specific for different positions and orientations of the wearable device comprising the acoustic physiological characteristic sensor.

As mentioned earlier, other examples of physiological characteristic sensor can include a muscle activity sensor for acquiring muscle activity signals (such as an electromyography EMG sensor for acquiring electromyography signals) a skin temperature sensor for acquiring skin temperature signals of the subject, and a respiratory rate sensor for acquiring respiratory rate signals of the subject.

In an embodiment where a wearable device comprises one (i.e. a single) physiological characteristic sensor, the wearable device may comprise a single electrocardiogram (ECG) physiological characteristic sensor, a single acoustic physiological characteristic sensor, or any other single physiological characteristic sensor such as those mentioned above. In an embodiment where the wearable device comprises more than one physiological characteristic sensor, the physiological characteristic sensors may all be of the same type of physiological characteristic sensor, some of the physiological characteristic sensors may be of the same type of physiological characteristic sensor (i.e. some of the physiological characteristic sensor may be of a different type of physiological characteristic sensor), or the physiological characteristic sensors may all be of different types of physiological characteristic sensor.

In embodiments where more than one physiological characteristic signal is acquired, the physiological characteristic signals may be acquired from the same physiological characteristic sensor. In other embodiments where more than one physiological characteristic signal is acquired, the physiological characteristic signals may be acquired from different physiological characteristic sensors. For example, the control unit 302 may be configured to acquire a first physiological characteristic signal by controlling a first physiological characteristic sensor to acquire the first physiological characteristic signal and may be configured to acquire a second physiological characteristic signal by controlling a second physiological characteristic sensor to acquire the second physiological characteristic signal. As mentioned earlier, the physiological characteristic sensors may be provided in a wearable device. The physiological characteristic sensors may be provided in the same wearable device or a different wearable device.

Although some examples have been provided above for wearable devices, physiological characteristic sensors, and their arrangements, those skilled in the art will be aware of wearable devices, physiological characteristic sensors and other types of wearable devices and physiological characteristic sensors that can be used and will also be aware of other arrangements for the wearable devices and physiological characteristic sensors.

Referring again to FIG. 3, in some embodiments, the apparatus 300 may comprise a memory unit 304 configured to store program code that can be executed by the control unit 302 to perform the method described herein. The memory unit 304 can also be used to store information, data, signals and measurements made or acquired by any sensors or devices that are part of the apparatus 300 or that are external to the apparatus 300 (such as any physiological characteristic sensors of one or more wearable devices).

In some embodiments, the apparatus 300 may comprise a communications interface component 306 for enabling the apparatus 300 to communicate with any sensors and devices (such as any physiological characteristic sensors of one or more wearable devices) that are external or internal to the apparatus 300. The communications interface component 306 may communicate with any sensors and devices wirelessly or via a wired connection.

In some embodiments, the apparatus 300 may comprise at least one user interface component 308 for use in providing the subject or other user of the apparatus 300 (for example, a care giver, a healthcare provider, a health coach, a family member, an emergency contact person, or any other person) with information resulting from the method according to the invention. The user interface component 308 can comprise any component that is suitable for providing the information resulting from the method according to the invention, and can be, for example, any one or more of a display screen or other visual indicator, a speaker, one or more lights, and a component for providing tactile feedback (e.g. a vibration function). The user interface component 308 may be or may comprise means that enables the subject or another user of the apparatus 300 to interact with and/or control the apparatus 300. For example, the user interface component 308 may comprise a switch, a button or other control means for controlling, activating and/or deactivating the apparatus 300 and/or the process of acquiring sensor signals.

It will be appreciated that FIG. 3 only shows the components required to illustrate this aspect of the invention, and in a practical implementation the apparatus 300 may comprise additional components to those shown. For example, the apparatus 300 may comprise a battery or other power supply for powering the apparatus 300 or means for connecting the apparatus 300 to a mains power supply.

Figure 4:
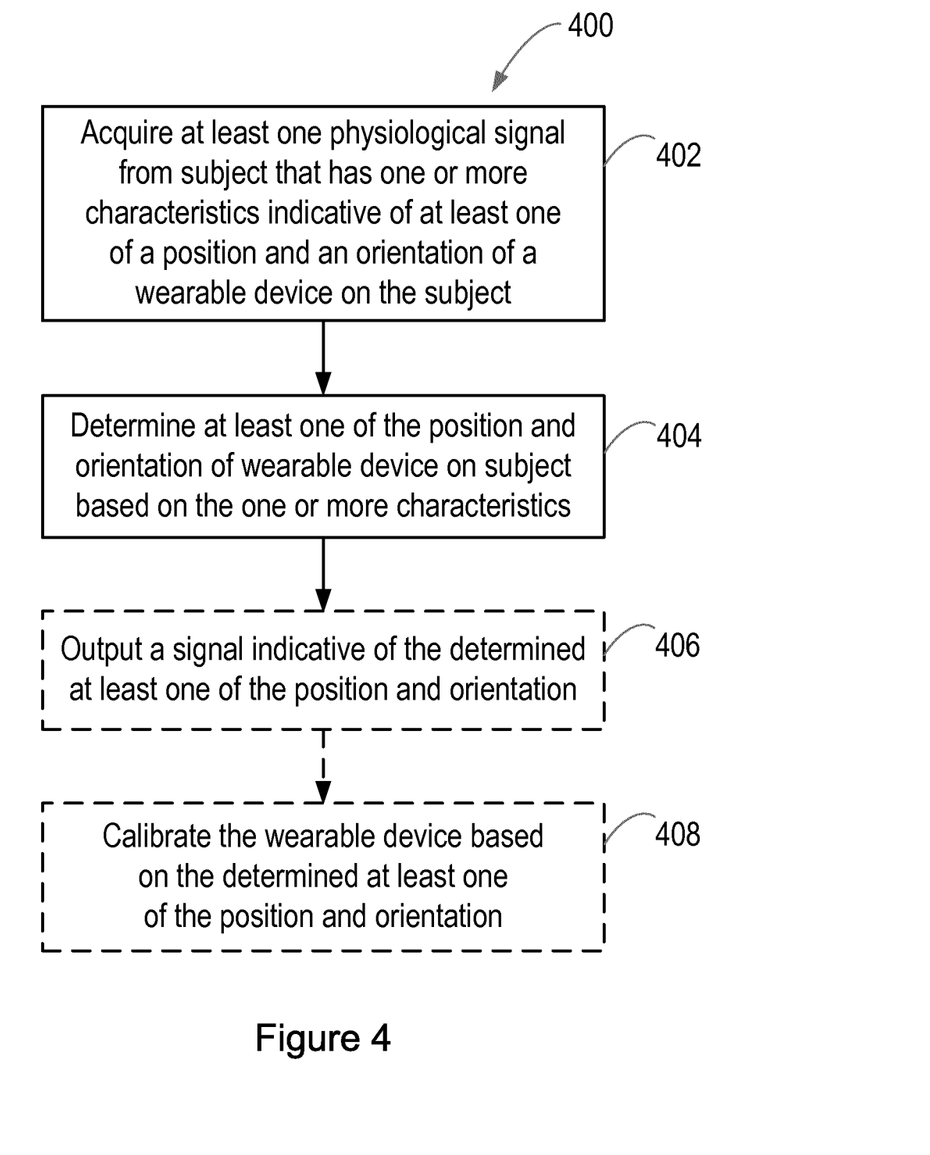
FIG. 4 is a flow chart illustrating a method according to an embodiment.
Figure 5A:
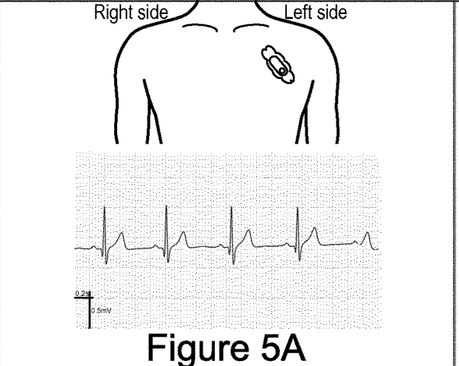
FIG. 5 is an illustration of an exemplary embodiment in which a wearable device is placed at different positions and orientations on a subject.
Figure 5B:
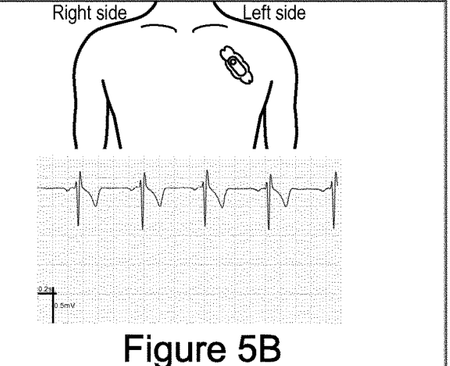
Figure 5C:
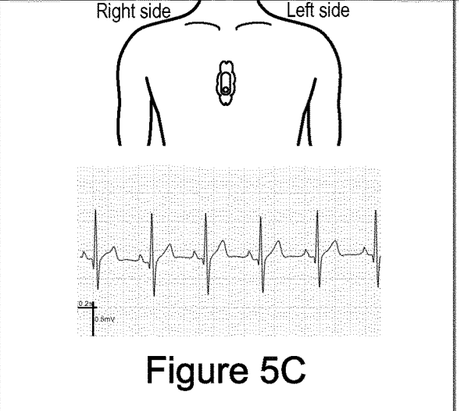
Figure 5D:
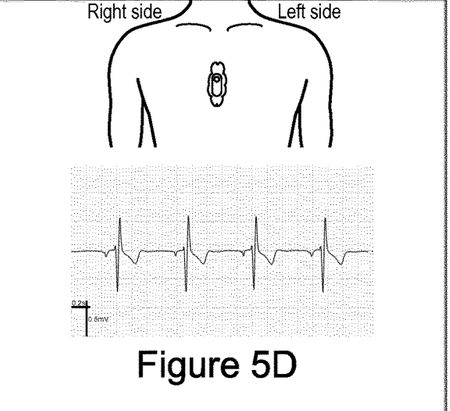
Figure 5E:
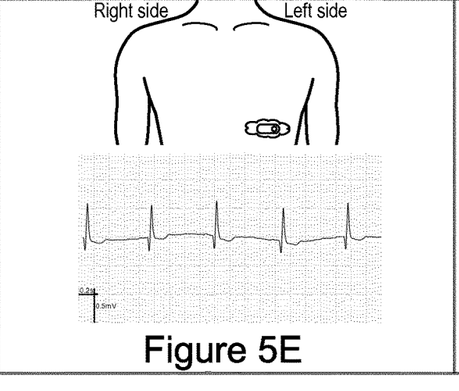
Figure 5F:
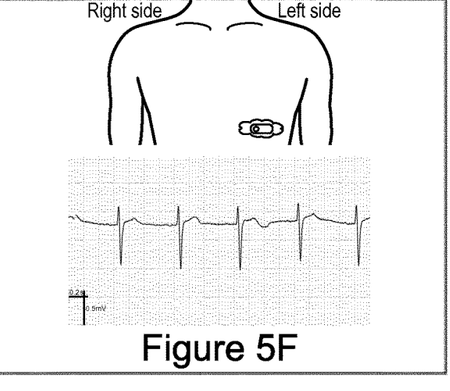

FIG. 4 illustrates a method 400 for determining at least one of a position and an orientation (i.e. a position and/or an orientation) of a wearable device on a subject according to an embodiment. More specifically, FIG. 4 illustrates a method of operating the apparatus 300 comprising the control unit 302 to determine the at least one of the position and orientation of the wearable device on the subject. The illustrated method 400 can generally be performed by or under the control of the control unit 302.

With reference to FIG. 4, at block 402, at least one physiological characteristic signal is acquired from the subject. The control unit 302 is configured to acquire the at least one physiological characteristic signal from the subject. For example, the control unit 302 may be configured to acquire the at least one physiological characteristic signal from the subject by controlling at least one physiological characteristic sensor of one or more wearable devices to acquire the at least one physiological characteristic signal in the manner described earlier.

The at least one physiological characteristic signal acquired from the subject is a physiological characteristic signal that has one or more characteristics indicative of at least one of a position and an orientation of a wearable device on the subject (i.e. indicative of a position and/or an orientation of a wearable device on a subject). In other words, the at least one physiological characteristic signal acquired has one or more characteristics specific to a certain position and orientation of a wearable device on the subject (i.e. the at least one physiological characteristic signal acquired has one or more characteristics, which are unique features that depend on the position and orientation of a wearable device on the subject).

At block 404, the at least one of the position and orientation (i.e. the position and/or the orientation) of the wearable device on the subject is determined based on the one or more characteristics indicative of the at least one of the position and orientation of the wearable device on the subject. In other words, the at least one of the position and orientation of the wearable device on the subject is extracted from the at least one physiological characteristic signal acquired from the subject by analysis of the one or more characteristics indicative of the at least one of the position and orientation of the wearable device on the subject. The control unit 302 is configured to determine the at least one of the position and orientation of the wearable device on the subject.

As mentioned earlier, in some embodiments, the at least one physiological characteristic signal can comprise an electrocardiogram physiological characteristic signal. With regard to an electrocardiogram physiological characteristic signal, the one or more characteristics indicative of the at least one of the position and orientation of the wearable device on the subject may comprise one or more of a morphology of the electrocardiogram signal, an amplitude of the electrocardiogram signal, and a polarity of the electrocardiogram signal. These characteristics are different for different positions and orientations on the body of the subject and can thus be used to determine the at least one of the position and orientation of the wearable device on the subject.

As also mentioned earlier, in some embodiments, the at least one physiological characteristic signal can comprise, or further comprise (for example, in addition to an electrocardiogram signal), an acoustic physiological characteristic signal. With regard to an acoustic physiological characteristic signal, the one or more characteristics indicative of the at least one of the position and orientation of the wearable device on the subject may comprise one or more of a frequency of the acoustic signal, a power of the acoustic signal, a phase of the acoustic signal, and a temporal feature of the acoustic signal. These characteristics are different for different positions and orientations on the body of the subject and can thus be used to determine the at least one of the position and orientation of the wearable device on the subject.

In some embodiments, the at least one of the position and orientation of the wearable device on the subject is determined by comparing the one or more characteristics of the at least one physiological characteristic signal acquired from the subject to a plurality of predefined (or pre-programmed) characteristics. The plurality of predefined characteristics are each associated with at least one of a predefined position and orientation of the wearable device. In other words, the plurality of predefined characteristics are specific to a particular at least one of a predefined position and orientation of the wearable device.

The predefined characteristics may be stored in a database (such as in the memory unit 304 of the apparatus 300). The predefined characteristics may be stored in a database following an initial calibration procedure in which physiological characteristic signals are acquired with the wearable device at different positions and orientations on the body of a subject. The predefined characteristics are stored with the corresponding position and orientation of the wearable device for those predefined characteristics for comparison with subsequently acquired physiological characteristic signals. In some embodiments, the predefined characteristics may be stored in the form of a look-up table to enable comparison of characteristics from acquired physiological characteristic signals with the predefined characteristics. In some embodiments, the predefined characteristics may be updated (i.e. a further calibration procedure may be performed) at set time intervals. In addition, or alternatively, the predefined characteristics may be updated upon receiving a user input to update the predefined characteristics.

In some embodiments, the predefined characteristics may be obtained from analysis of (e.g. characteristic feature extraction from) physiological characteristic signals acquired from a plurality of subjects for which the wearable device is placed at a plurality of different positions and orientations on the subject. The predefined characteristics can be used to train a classifier to automatically recognise the at least one of the position and orientation.

Thus, based on a comparison of the one or more characteristics of the at least one physiological characteristic signal acquired from the subject with the plurality of predefined characteristics, the at least one of the position and orientation of the wearable device on the subject can be determined. In some embodiments, it may be determined which of the plurality of predefined characteristics match or most closely match the one or more characteristics of the acquired at least one physiological characteristic signal. In this example, the at least one of the position and orientation of the wearable device on the subject is determined as the at least one of the predefined position and orientation associated with the predefined characteristics determined to match or most closely match the one or more characteristics of the acquired at least one physiological characteristic signal.

In some embodiments, the at least one of the position and orientation of the wearable device on the subject is determined based on the comparison by interpolating the plurality of predefined characteristics and the at least one of the associated predefined positions and orientations of the wearable device to determine the at least one of the position and orientation of the wearable device on the subject. For example, intermediate position and orientation combinations of the wearable device can be determined through an interpolation of predefined characteristics and associated predefined position and orientation combinations. In this way, it is possible to determine more positions and orientations than those that are predefined.

In some embodiments, a motion signal (such as an acceleration signal) may also be acquired from the subject. For example, the control unit 302 may be configured to control one or more motion sensors to acquire at least one motion signal (or acceleration signal) from the subject. Examples of motion sensors include an accelerometer, a gyroscope, a magnetometer, a camera, or any other motion sensor, or combination of motion sensors. One or more wearable devices may comprise the one or more motion sensors and the one or more physiological characteristic sensors. In these embodiments, the at least one of the position and orientation of the wearable device on the subject may be determined based on the one or more characteristics (of at least one acquired physiological characteristic signal acquired from the subject) indicative of the at least one of the position and orientation of the wearable device on the subject and the acquired at least one motion signal (or acceleration signal) from the subject. In this way, it is possible to obtain a more accurate and reliable determination of the at least one of the position and orientation of the wearable device on the subject.

In some embodiments, a pressure signal may also be acquired from the subject. For example, the control unit 302 may be configured to control one or more pressure sensors to acquire at least one pressure signal from the subject. Examples of pressure sensors include an air pressure sensor, a barometer, or any other pressure sensor, or combination of pressure sensors. One or more wearable devices may comprise the one or more pressure sensors and the one or more physiological characteristic sensors. In these embodiments, the at least one of the position and orientation of the wearable device on the subject may be determined based on the one or more characteristics (of at least one physiological characteristic signal acquired from the subject) indicative of the at least one of the position and orientation of the wearable device on the subject and the acquired at least one pressure signal from the subject. In this way, it is possible to obtain a more accurate and reliable determination of the at least one of the position and orientation of the wearable device on the subject.

In some embodiments, one or more wearable devices may comprise at least one physiological characteristic sensor, at least one motion sensor and at least one pressure sensor. In these embodiments, the at least one of the position and orientation of the wearable device on the subject may be determined based on the one or more characteristics (of at least one physiological characteristic signal acquired from the subject) indicative of the at least one of the position and orientation of the wearable device on the subject, an acquired at least one motion signal from the subject, and an acquired at least one pressure signal from the subject. In this way, it is possible to obtain an even more accurate and reliable determination of the at least one of the position and orientation of the wearable device on the subject.

At block 406, in some embodiments, a signal indicative of the determined at least one of the position and orientation of the wearable device on the subject may be output. For example, the signal indicative of the determined at least one of the position and orientation of the wearable device on the subject may be output via the at least one user interface component 308 of the apparatus 300. This output may be via any suitable component such as any one or more of a display screen or other visual indicator, a speaker, one or more lights, and a component for providing tactile feedback (e.g. a vibration function).

At block 408, in some embodiments, the wearable device may be calibrated based on the determined at least one of the position and orientation of the wearable device on the subject. In some embodiments, the determined at least one of the position and orientation of the wearable device on the subject can be used to determine other parameters or information. For example, the determined at least one of the position and orientation of the wearable device on the subject can be used in a posture algorithm (for example, to determine lying position such as for the prevention of decubitus), in an energy expenditure measurement, as a calibration constant in the measurement of arterial oxygen saturation (SpO2) adapted automatically to body location, to analyse the gait of the subject from trunk-accelerometry during shuffling or walking in different orthogonal directions (such as mediolateral, anteroposterior, vertical), as a calibration constant for temperature measurements, or in adapting an algorithm for extracting respiration signal (for example, at some body locations respiration based on bioimpedance, accelerometer and PPG can be combined to provide a more accurate measurement, whereas at other locations one or more signals can be omitted to decrease a signal-to-noise ratio).

FIG. 5 is an illustration of exemplary embodiment in which a wearable device is placed at different positions and orientations on a subject and an associated electrocardiogram (ECG) signal is acquired from an ECG sensor integrated in the wearable device. In this exemplary embodiment, the at least one of the position and orientation of the wearable device on the subject is determined based on the acquired ECG signal from a subject. In other words, the at least one of the position and orientation of the wearable device on the subject is extracted from an ECG signal acquired from a subject.

The ECG sensor in this exemplary embodiment is in the form of two electrodes. However, it will be understood that any other number of electrodes can also be used. The more electrodes that are used, the more easily and accurately the at least one of the position and orientation of the wearable device on the subject can be determined.

FIGS. 5A-5F illustrate the wearable device applied to the subject in six different ways together with the associated ECG signals. Specifically, FIGS. 5A-5F illustrate the wearable device applied to the subject at three different positions and in two different orientations (where the orientation can be seen from the position of a marker provided on the wearable device). As illustrated in FIGS. 5A-5F, the ECG signals acquired for each of the six different ways in which the wearable device is applied to the subject are specific to the position and orientation of the wearable device on the subject for that ECG signal.

In order to determine at least one of the position and orientation of a wearable device on a subject, one or more characteristics of at least one ECG signal acquired from the wearable device on the subject are compared to predefined characteristics of an ECG signal. The predefined characteristics of the ECG signal may be stored in a database (such as in the memory unit 304 of the apparatus 300). In some embodiments, the predefined characteristics may be stored in a database following an initial calibration procedure in which an ECG signal is acquired with the wearable device at each position and orientation on the body of a subject for subsequent comparison with acquired ECG signals. In other embodiments, another calibration procedure may be implemented. For example, a two dimensional (2D) ECG vector may be determined from a 12-lead ECG and an acquired ECG signal may then be projected on the 2D ECG vector of the wearable device to provide the at least one of the position and orientation of the wearable device. This can be useful for a subject that is moved from a high acuity setting (such as an intensive care unit in which a full 12-lead ECG may be used) to a low acuity setting (such as a general ward or home care) where a wearable device is sufficient.

The comparison of one or more characteristics of the at least one ECG signal acquired from the wearable device on the subject to the predefined characteristics of an ECG signal may involve any comparison suitable to determine at least one of the position and orientation of the wearable device on the subject.

Figure 6:
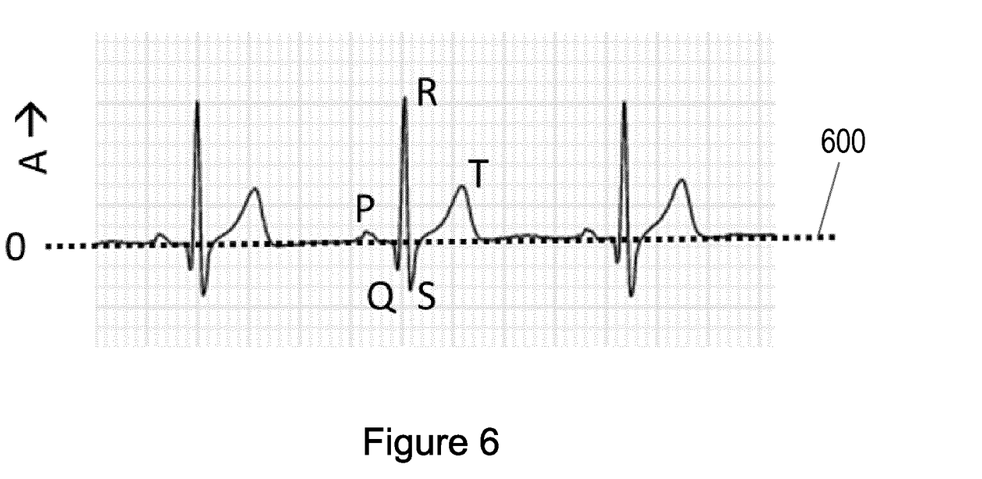
FIG. 6 is an illustration of predefined characteristics of an electrocardiogram signal.

FIG. 6 illustrates an example of predefined characteristics of an electrocardiogram (ECG) signal. An exemplary embodiment will now be described for the comparison of one or more characteristics of at least one ECG signal acquired from the wearable device on the subject to the predefined characteristics of an ECG signal.

In this embodiment, the locations of at least some of the ECG peaks shown in FIG. 6 (such as at least part of the PQRST pattern of the ECG signal) are detected in the acquired ECG signal. For example, the location of the Q, R and S peaks of FIG. 6 may be detected in the acquired ECG signal. Although an example is provided, it will be understood that the location of any other peaks or combination of peaks in the acquired ECG signal may be detected. Those skilled in the art will be aware of suitable techniques that can be used to detect the locations of ECG peaks in the acquired ECG signal.

Then, the amplitudes of the detected ECG peaks are determined relative to a baseline value 600. The baseline value 600 may, for example, be determined using median filtering or any other technique suitable for determining an ECG baseline. A peak amplitude ratio of the acquired ECG signal may then be determined. For example, where the location of the Q, R and S peaks of FIG. 6 are detected in the acquired ECG signal and the amplitude of those peaks are determined, the peak amplitude ratio may be determined as follows:

Peak Amplitude Ratio=Abs($AS-AQ$)/Abs($AR-AQ$), where As is the determined amplitude of the S peak detected in the acquired ECG signal, AQ is the determined amplitude of the Q peak detected in the acquired ECG signal, and AR is the determined amplitude of the R peak detected in the acquired ECG signal. In other words, the peak amplitude ratio for the acquired ECG signal may be determined as the ratio of the absolute value of the difference between the determined amplitude of the S peak and the determined amplitude of the Q peak of the acquired ECG signal to the absolute value of the difference between the determined amplitude of the R peak and the determined amplitude of the Q peak of the acquired ECG signal.

The determined peak amplitude ratio is then compared to a plurality of predefined peak amplitude ratios, where the plurality of predefined peak amplitude ratios are associated with at least one of a position and orientation of the wearable device on a subject. In other words, the determined peak amplitude ratio is a characteristic of the acquired at least one physiological characteristic signal that is compared to predefined characteristics (or predefined peak amplitude ratios). The predefined characteristics may be stored in the form of a look-up table with the associated positions and orientations. An example of a look-up table is provided below.

| Location and Orientation | AT | AR | Abs(AS − AQ)/Abs(AR − AQ) |
|---|---|---|---|
| A1 | >0 | >0 | <TH |
| A2 | <0 | <0 | <TH |
| B1 | >0 | >0 | >TH |
| B2 | <0 | <0 | >TH |
| C1 | <0 | >0 | <TH |
| C2 | >0 | <0 | <TH |

Here, the predefined characteristics comprise the determined amplitude of the T peak detected in the acquired ECG (AT), the determined amplitude of the R peak detected in the acquired ECG (AR), and the peak amplitude ratio (Abs(AS− AQ)/Abs(AR−AQ)).

In this example, it is determined whether the amplitude of the T peak detected in the acquired ECG is greater than zero or less than zero. Similarly, it is determined whether the amplitude of the R peak detected in the acquired ECG is greater than zero or less than zero. It is also determined whether the peak amplitude ratio is more than a threshold value or less than a threshold value. Based on these determinations, the look-up table is searched to find a row of predefined characteristics that match those characteristics determined from the acquired at least one physiological characteristic signal. Each row in the look-up table is unique and mutually exclusive. The position and orientation of the wearable device on the subject that is associated with the matched predefined characteristics can thus be extracted from the look-up table.

The locations and orientations provided in the look-up table correspond to the locations and orientations of the wearable device on the subject, as illustrated in FIGS. 5A-5F. Specifically, the location and orientation denoted by A1 in the table corresponds to the location and orientation illustrated in FIG. 5A, the location and orientation denoted by A2 in the table corresponds to the location and orientation illustrated in FIG. 5B, the location and orientation denoted by B1 in the table corresponds to the location and orientation illustrated in FIG. 5C, the location and orientation denoted by B2 in the table corresponds to the location and orientation illustrated in FIG. 5D, the location and orientation denoted by C1 in the table corresponds to the location and orientation illustrated in FIG. 5E, and the location and orientation denoted by C2 in the table corresponds to the location and orientation illustrated in FIG. 5F.

In this way, it is possible to determine the at least one of the position and orientation of the wearable device on the subject for each ECG signal.

Figure 7:
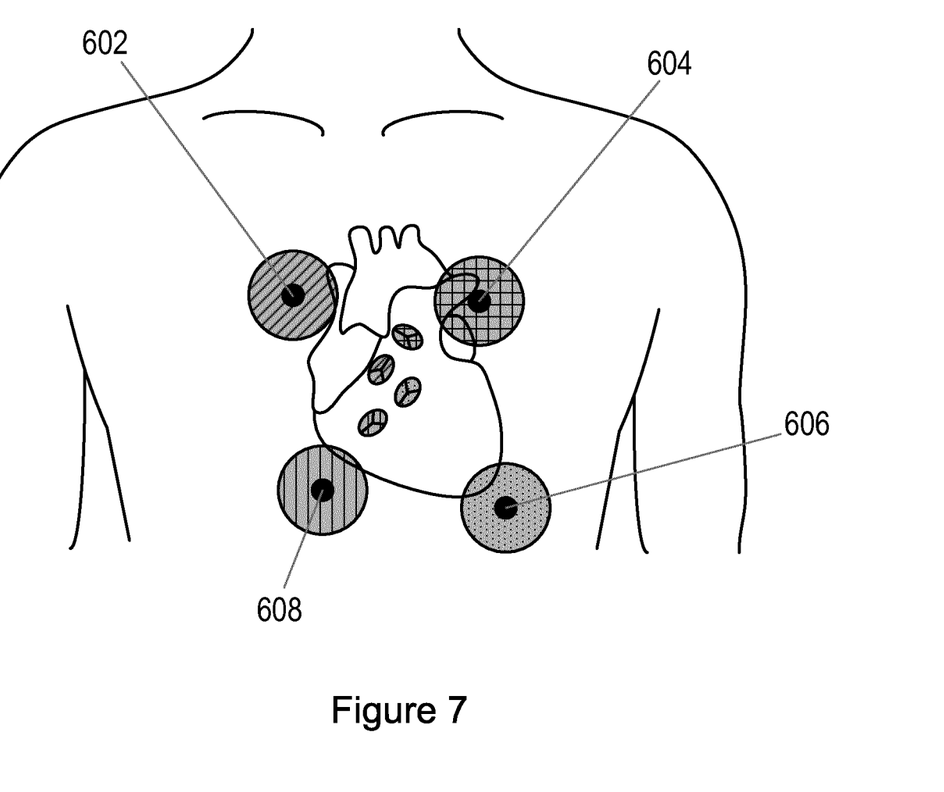
FIG. 7 is an illustration of another exemplary embodiment in which a wearable device is placed at different positions and orientations on a subject.

FIG. 7 is an illustration of exemplary embodiment in which an array (or plurality) of acoustic (or vibration detection) sensors 602, 604, 606, 608 of a wearable device are worn by a subject and one or more acoustic physiological characteristic signals are acquired from the acoustic sensors of the wearable device. The one or more acoustic physiological characteristic signals may be acquired from one or more of the acoustic sensors. Examples of an acoustic sensor include accelerometers, microphones, electromechanical film sensors, or any other acoustic physiological characteristic sensors. An array of acoustic sensors may comprise a combination of one or more types of acoustic sensor. The acoustic sensors can detect sounds (for example, murmurs) from the body of the subject and thus can acquire acoustic signals.

In this exemplary embodiment, the at least one of the position and orientation of the wearable device on the subject is determined based on the one or more acquired acoustic physiological characteristic signals from a subject. In other words, the at least one of the position and orientation of the wearable device on the subject is extracted from the one or more acoustic physiological characteristic signals acquired from the subject. For example, an acquired acoustic physiological characteristic signal has distinct characteristics that can be used to determine the position and orientation of the wearable device on the body of the subject. In this exemplary embodiment, the acoustic sensors 602, 604, 606, 608 of the wearable device are placed near the heart of the subject (as shown in FIG. 7). In order to determine the at least one of the position and orientation of the wearable device on the subject, the acquired acoustic physiological characteristic signals can be compared to a recording of a heart sound (such as a phonocardiography or PCG signal) made during a cardiac cycle.

Figure 8:
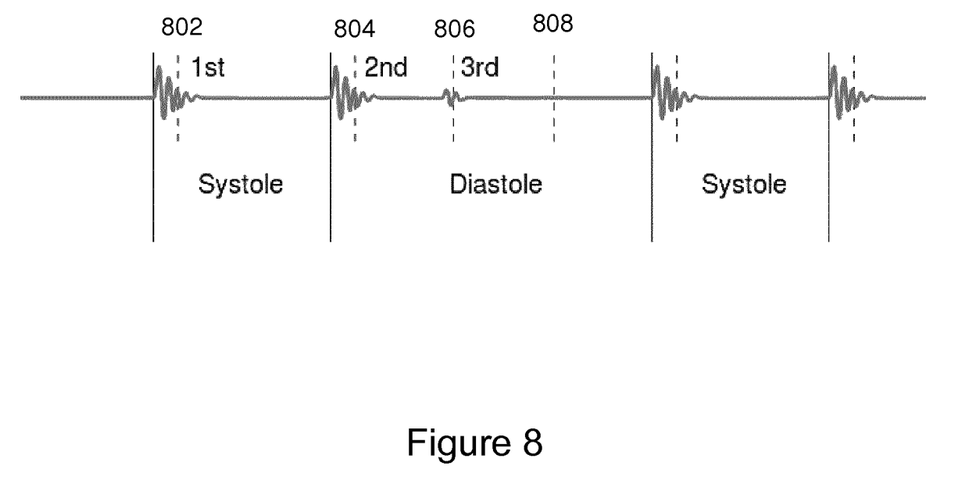
FIG. 8 is an illustration of predefined characteristics of a phonocardiography signal.

FIG. 8 illustrates an example of predefined characteristics of a phonocardiography (PCG) signal. The acoustic signals acquired from the heart of the subject by one or more acoustic sensors (such as the acoustic sensors 602, 604, 606 and 608 shown in FIG. 7) can be compared to the predefined characteristics of the PCG signal.

A PCG signal can have four distinct sounds due to vibrations created by the movement of the heart valves. With reference to FIG. 8, a first sound 802 occurs when the atrioventricular valves close at the beginning of the systole period, a second sound 804 occurs when the aortic valve and pulmonary valve close at the end of the systole period, a third sound 806 occurs due to the vibration of ventricular valves as a result of the first rapid filling during the diastole period, and a fourth sound 808 occurs when atria contract during second phase of ventricular filling.

The predefined characteristics of a PCG signal and predefined values for the distance between the valves of the heart can be used to determine the position and orientation of the wearable device on the subject. The predefined characteristics of a PCG signal can include the periodicity of the signals and the order of the signals (which is indicative of the order of the heart valves opening and closing). In one example, a near-field source localization technique may be used to determine a distance and an angle between the wearable device and parts of the heart in order to determine the position and orientation of the wearable device on the subject. An example of a near-field source localization technique that may be used is a multiple signal classification (MUSIC) technique. However, it will be appreciated that other localization techniques can be used.

In some embodiments, an electrocardiogram (ECG) signal may be used to identify the components of the heart sounds of a phonocardiography (PCG) signal. For example, an R peak of an ECG signal can be identified and used to identify the components of the heart sounds of a PCG signal since the R peak of an ECG signal corresponds to the first sound 802 at the beginning of the systole period of a PCG signal.

In some embodiments, the at least one of the position and orientation of the wearable device on the subject may be determined based on more than one type of physiological characteristic signal (i.e. from a combination of different physiological characteristic signals) acquired from the wearable device on the subject. For example, the at least one of the position and orientation of the wearable device on the subject may be determined based on both an acoustic physiological characteristic signal acquired from a subject and an ECG physiological characteristic signal acquired from the subject or any other combination of different physiological characteristic signals acquired from the subject. Also, in some embodiments, the at least one of the position and orientation of the wearable device on the subject may be determined based on one or more types of physiological characteristic signal and an acceleration signal acquired from the wearable device on the subject. In this way, the reliability and accuracy of the determined at least one of the position and orientation of the wearable device can be improved even further.

There is thus provided an improved method and apparatus that more reliably and accurately determines at least one of a position and an orientation of a wearable device on a subject. This can be beneficial in many situations including in the monitoring of a subject at home and in the monitoring of a subject at a professional healthcare facility (such as a hospital).

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of operating an apparatus comprising a control unit to determine a position and an orientation of a wearable device on a subject, the method comprising:
   acquiring, by the control unit, at least one physiological characteristic signal from a subject, the at least one physiological characteristic signal acquired from the subject having one or more characteristics indicative of a position and an orientation of a wearable device on the subject, wherein the position is where the apparatus is applied on a body of the subject and the orientation indicates positions of electrodes of the apparatus relative to each other; and
   determining, by the control unit, the position and orientation of the wearable device on the subject based on the one or more characteristics indicative of the position and orientation of the wearable device on the subject,
   wherein determining the position and orientation of the wearable device on the subject comprises:
   comparing the one or more characteristics of the acquired at least one physiological characteristic signal from the subject to a plurality of predefined characteristics, each of the plurality of predefined characteristics associated with a predefined position and orientation of the wearable device; and
   determining the position and orientation of the wearable device on the subject based on the comparison.

2. A method according to claim 1, wherein determining the position and orientation of the wearable device on the subject based on the comparison comprises:
   determining which of the plurality of predefined characteristics match or most closely match the one or more characteristics of the acquired at least one physiological characteristic signal; and
   determining the position and orientation of the wearable device on the subject as the predefined position and orientation associated with the predefined characteristics determined to match or most closely match the one or more characteristics of the acquired at least one physiological characteristic signal.

3. A method according to claim 1, wherein the position and orientation of the wearable device on the subject based on the comparison comprises:
   interpolating the plurality of predefined characteristics and the associated predefined positions and orientations of the wearable device to determine the at least one of the position and orientation of the wearable device on the subject.

4. A method according to claim 1, wherein the at least one physiological characteristic signal comprises an electrocardiogram signal.

5. A method according to claim 4, wherein the one or more characteristics indicative of the position and orientation of the wearable device on the subject comprises one or more of:
   a morphology of the electrocardiogram signal;
   an amplitude of the electrocardiogram signal; and
   a polarity of the electrocardiogram signal.

6. A method according to claim 1, further comprising:
   outputting a signal indicative of the determined position and orientation of the wearable device on the subject.

7. A method according to claim 1, further comprising:
   calibrating the wearable device based on the determined position and orientation of the wearable device on the subject.

8. A computer program product comprising a computer readable medium, the computer readable medium having computer readable code embodied therein, the computer readable code being configured such that, on execution by a suitable computer or processor, the computer or processor is caused to perform the method of claim 1.

9. A method according to claim 1, wherein the orientation is determined by a polarity of the electrocardiogram signal.

10. A method of operating an apparatus comprising a control unit to determine a position and an orientation of a wearable device on a subject, the method comprising:
   acquiring, by the control unit, at least one physiological characteristic signal from a subject, the at least one physiological characteristic signal acquired from the subject having one or more characteristics indicative of a position and an orientation of a wearable device on the subject, wherein the position is where the apparatus is applied on a body of the subject and the orientation indicates positions of electrodes of the apparatus relative to each other; and
   determining, by the control unit, the position and orientation of the wearable device on the subject based on the one or more characteristics indicative of the position and orientation of the wearable device on the subject,
   wherein the at least one physiological characteristic signal comprises, or further comprises, an acoustic signal derived from a number of sounds produced by the subject.

11. A method according to claim 10, wherein the one or more characteristics of the acoustic signal indicative of the position and orientation of the wearable device on the subject comprises one or more of:
   a frequency of the acoustic signal;
   a power of the acoustic signal;
   a phase of the acoustic signal; and
   a temporal feature of the acoustic signal.

12. An apparatus for determining a position and an orientation of a wearable device on a subject, the apparatus comprising:
   a control unit configured to:
   acquire at least one physiological characteristic signal from a subject, the acquired at least one physiological characteristic signal from the subject having one or more characteristics indicative of a position and an orientation of a wearable device on the subject, wherein the position is where the apparatus is applied on a body of the subject and the orientation indicates positions of electrodes of the apparatus relative to each other; and
   determine the position and orientation of the wearable device on the subject based on the one or more characteristics indicative of the position and orientation of the wearable device on the subject,
   wherein the position and orientation of the wearable device on the subject is determined at least by:
   comparing the one or more characteristics of the acquired at least one physiological characteristic signal from the subject to a plurality of predefined characteristics, each of the plurality of predefined characteristics associated with a predefined position and orientation of the wearable device; and
   determining the position and orientation of the wearable device on the subject based on the comparison.

13. An apparatus according to claim 12, wherein the control unit is configured to acquire the at least one physiological characteristic signal from the subject by controlling at least one physiological characteristic sensor to acquire the at least one physiological characteristic signal.

14. An apparatus according to claim 13, wherein the wearable device comprises the at least one physiological characteristic sensor.

15. An apparatus according to claim 14, wherein the at least one physiological characteristic sensor comprises one or more of:
   an electrocardiogram physiological characteristic sensor; and
   an acoustic physiological characteristic sensor.

* * * * *